United States Patent [19]

Bell et al.

[11] Patent Number: 4,604,346

[45] Date of Patent: Aug. 5, 1986

[54] SKIN-EQUIVALENT PREPARED BY THE USE OF PUNCH BIOPSY

[75] Inventors: Eugene Bell, Dedham, Mass.; Louis Dubertret, Paris, France

[73] Assignee: Massachusetts Institute of Technology, Cambridge, Mass.

[21] Appl. No.: 658,499

[22] Filed: Oct. 9, 1984

[51] Int. Cl.⁴ ............................................. A01N 1/02
[52] U.S. Cl. ..................................................... 435/1
[58] Field of Search ...................... 435/1, 240; 424/95

[56] References Cited

U.S. PATENT DOCUMENTS

| | | | |
|---|---|---|---|
| 4,299,819 | 11/1981 | Eisinger | 435/1 |
| 4,391,909 | 7/1983 | Lim | 435/1 |
| 4,439,521 | 3/1984 | Archer et al. | 435/1 |

Primary Examiner—Sam Rosen
Attorney, Agent, or Firm—Hamilton, Brook, Smith and Reynolds

[57] ABSTRACT

An improvement in the preparation of living skin-equivalents from contracted hydrated collagen lattices having keratinocyte cells on the surface is disclosed herein. In this improvement, punch biopsies of skin are employed to provide a source of keratinocyte cells to the lattices.

10 Claims, 2 Drawing Figures

SKIN-EQUIVALENT PREPARED BY THE USE OF PUNCH BIOPSY

DESCRIPTION

1. Technical Field

This invention is in the fields of biology and medicine and particularly relates to the preparation of a living skin-equivalent which can be used to replace removed or damaged skin, particularly in human beings.

2. Background Art

U.S. Ser. No. 381,978 now U.S. Pat. No. 4,485,096, filed May 26, 1982, describes methods by which living tissue-equivalents can be formed. These living tissue-equivalents are produced by forming hydrated collagen lattices, in vitro. Such lattices are contracted into living tissue-equivalents employing contractile agents incorporated into the lattices. Examples of contractile agents include fibroblast cells and blood platelets.

Skin-equivalents are described in Ser. No. 381,978 now U.S. Pat. No. 4,485,096 which are produced by plating keratinocyte cells on dermal-equivalents formed from hydrated collagen lattices contracted with a contractile agent. These skin-equivalents are uniquely different from previously described artificial skin because their basic organization is like that of skin and their living constituent cells may even be donated by a potential graft recipient.

SUMMARY OF THE INVENTION

The present invention is based upon the discovery that skin-equivalent can be formed by modifying the procedures disclosed in Ser. No. 381,978 now U.S. Pat. No. 4,485,096. In the modified procedures, punch biopsies of skin are incorporated into dermal-equivalent as a source of keratinocyte cells. It has now been found that such procedures result in excellent overgrowth of the dermal-equivalent by keratinocyte cells.

The use of punch biopsies as a technique for supplying keratinocyte cells has advantages, in many cases, over the previously employed technique of plating keratinocyte cells on the dermal-equivalent. Such advantages include the fact that a differentiated epidermis can be formed in a relatively short period of time. Additionally, a small punch biopsy of skin, e.g. 2 millimeters, can be employed to cover a large area, e.g. 1 square centimeter (a 50 time amplification). The area of a graft prepared by these techniques can be great because a number of punch biopsies can be inserted into a dermal-equivalent. Such punch biopsies can be inserted at the time that the dermal-equivalent is formed, or at a subsequent time.

Overgrowth of the punch biopsy is itself a selection process since only keratinocyte cells overgrow the dermal equivalent. The overgrowth is free of dendritic cells.

The skin-equivalent formed by the use of punch biopsies may itself provide a source of material useful for production of additional skin-equivalents. In other words, punch biopsies from a skin-equivalent may be employed in the production of other skin-equivalents.

From the experimental results obtained, it also appears that the stratum corneum that develops from skin-equivalents employing punch biopsies of skin is very similar to a normal stratum corneum.

In many cases, the dermal/epidermal adherence appears to be improved when punch biopsies of skin are employed compared to the previously employed plating techniques.

The punch biopsy method also accommodates well for application of other cells to the skin-equivalents. For example, pigment cells, called melanocytes, have been applied to the exposed surface of dermal-equivalent before they are overgrown with keratinocyte cells emanating from the punch biopsies. Experimentally, it has been shown that the keratinocytes cover the melanocytes as they form a continuous layer of cells over the dermal equivalent. The melanocytes become functional and contribute pigment to the keratinocyte layer.

The use of punch biopsies for epidermalizing the surface of dermal-equivalents also allows the immediate therapeutic clinical use of the skin-equivalents. Dermal-equivalents can be cryopreserved and held ready to receive punch biopsies for epidermalization at any time. The method is also very convenient for quantitative study of dermal/epidermal interactions and for pharmacological testing.

BEST MODE FOR CARRYING OUT THE INVENTION

Figure 1:
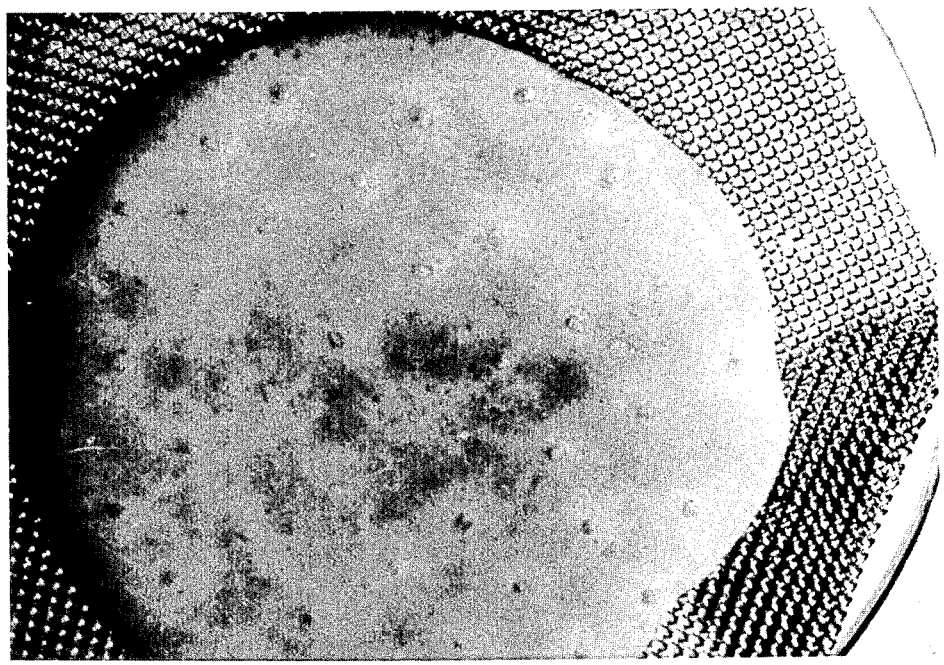
FIG. 1 is a photograph of a skin-equivalent prepared according to this invention.

The techniques of this invention are modifications of the basic techniques employed in producing skin-equivalents by the methods described in Ser. No. 381,978 now U.S. Pat. No. 4,485,096. Therefore, the teachings in Ser. No. 381,978 now U.S. Pat. No. 4,485,096 relating to the preparation of skin-equivalents are hereby incorporated into this application by reference.

The techniques of Ser. No. 581,978 now U.S. Pat. No. 4,485,096 will now be discussed briefly.

Hydrated collagen lattices are prepared employing collagen derived from rat tail tendon, calf skin collagen, or other sources. Solutions of collagen are prepared and maintained under slightly acidic conditions. Lattices are formed by adding fibroblast cells, or other contractile agents, with nutrient medium and base which raises the pH sufficiently to induce fibrillogenesis and gel formation.

Fibroblast cells, one example of a contractile agent, can be obtained from human skin or from any human or animal tissue. A convenient technique for forming the lattice containing cells involves neutralizing an acidic collagen solution and rapidly combining it with cells and nutrient medium. Upon neutralization, collagen fibrils form and the lattice gels with fibroblast cells homogeneously dispersed therethrough. The cells and collagen lattice are then maintained under conditions which allow the cells to attach to the collagen lattice and to contract it to a fraction of its original size, thereby providing the dermal-equivalent. There are other contractile agents, in addition to fibroblast cells. These include smooth muscle cells, striated muscle cells and heart muscle cells.

Another contractile agent is blood platelets, which in many cases, can be obtained from the blood of a potential tissue-equivalent recipient. Platelets are separated from whole blood by centrifugation or other techniques for separating blood components from whole blood.

As described above, overgrowth of the dermal-equivalent by keratinocyte cells is achieved according to this invention employing punch biopsies of skin. Such punch-biopsies can be obtained from the skin of a mouse, rat or human being, for example. These are typically obtained using cylindrical stainless steel punches which are typically in sizes of 2 or 4 mm in diameter. Punch biopsies are now routinely taken from human subjects for physiopathological or therapeutic uses. The skin biopsies taken with the punch can be incorporated into the dermal-equivalent lattice when it is poured.

The biopsy is positioned so that the epidermis can grow out at the level of the upper surface of the dermal-equivalent. The biopsy is held in place because the surrounding collagen lattice is contracted by the fibroblasts or other contractile agent.

Inserting the biopsy at the center of the dermal-equivalent results in radial outgrowth which covers the dermal-equivalent. Outgrowth occurs as a circular sheet that consists of multiple layers of keratinocyte cells. All phases of keratinocyte differentiation are represented in the epidermis, even close to the growing edge including a morphologically normal stratum corneum. The granular layer of the differentiated epidermis contains membrane coating granules (Odlund granules) as observed in the epidermis, in vivo. Normal epidermis differentiation is also evidenced by the presence of the 67k dalton keratin in extracts of the newly formed epidermis.

Overgrowth of a 5.5 cm diameter dermal-equivalent, before contraction of the lattice, by primary cells from a punch biopsy taken from a human or animal donor takes about 10 days in a typical case. For contrast, plated keratinocyte cells sometimes cover a dermal-equivalent of the same size in a shorter time, e.g., 4-7 days, but the coverage is not always multi-layered and is sometimes incomplete.

Keratinocyte cells from the primary biopsy have been subcultivated by taking punch biopsies from the skin-equivalent, in vitro. These starters of subcultures are handled in the same way as the original punch biopsies and are embedded in newly cast dermal-equivalents. By reducing the $Ca^{++}$ concentration to $0.05 \times 10^{-3}$ M, the rate of growth of epidermis from the punch is speeded up but an upshift to $1.5-2.0 \times 10^{-3}$ M $Ca^{++}$ is needed to simulate differentiation and keratinization.

In one series of experiments, a total of 80 skin-equivalents were fabricated employing punch biopsies from rat and mouse skin. Half were constituted with punch biopsies of 2.0 mm diameter, and the other half with punches of 4.0 mm diameter.

Another series of experiments employed 2.0 mm punch biopsies from donated human foreskin, while still yet another employed punches from the thigh region of a human donor who was the graft recipient, i.e. the recipient of the skin-equivalent constituted with autogenous cells. However, allogenic cells can also be used.

FIG. 1 is a photograph of a skin-equivalent constituted with punch biopsies which serve as a source of keratinocyte cells that grow out and over the underlying dermal-equivalent. The punch biopsies were taken from a human donor. Each punch is surrounded by a halo that signifies the presence of a radially expanding epidermis.

Figure 2:
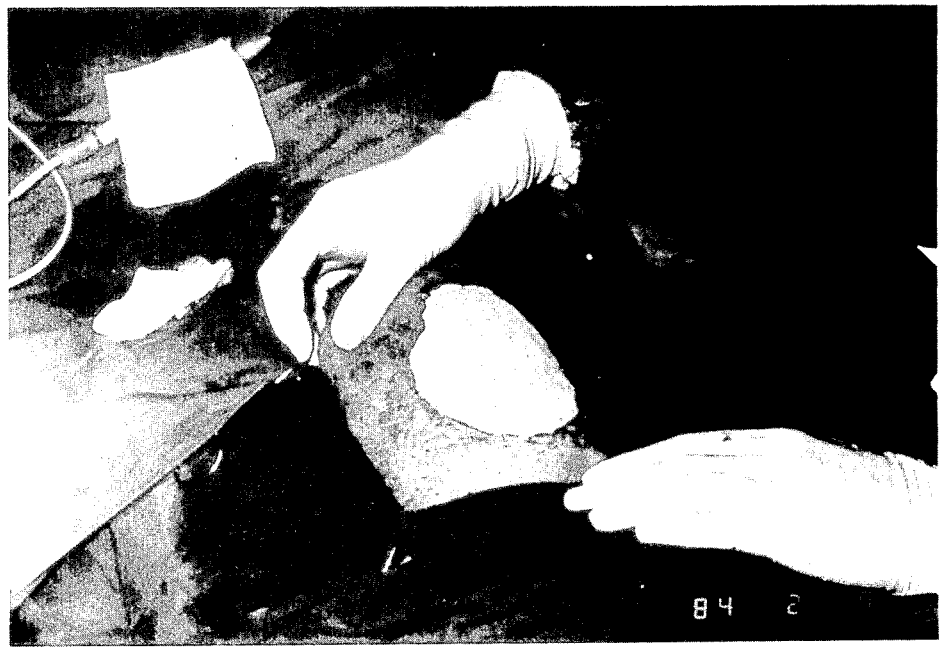
FIG. 2 is a photograph illustrating application of a skin-equivalent according to this invention to a recipient.

FIG. 2 is a photograph of a skin-equivalent being applied to a human patient.

INDUSTRIAL APPLICABILITY

The skin-equivalent described herein is suitable for the treatment of a wound to the skin of a human being or other mammal. It is particularly suitable for treating massive burns and for treatment of a variety of genetic and other disorders that require skin replacement.

EQUIVALENTS

Those skilled in the art will recognize, or be able to ascertain using no more than routine experimentation, other equivalents for the specific materials and steps described herein. Such equivalents are intended to be included within the scope of the following claims.

We claim:
1. A method of forming a skin-equivalent, comprising:
   a. forming an acidic solution of collagen;
   b. combining contractile cells and nutrient medium with said acidic solution of collagen;
   c. raising the pH of said solution of collagen to a level sufficient to precipitate collagen fibrils into a hydrated collagen lattice containing said contractile cells;
   d. incorporating one or more punch biopsies of skin into said hydrated collagen lattice; and
   e. maintaining said hydrated collagen lattice containing said punch biopsies under conditions sufficient for the contractile cells to contract the hydrated collagen lattice into a dermal-equivalent and sufficient to allow keratinocyte cells from said punch biopsies to overgrow the surface of said dermal equivalent thereby producing a skin-equivalent.

2. A method of claim 1 wherein steps b and c are done simultaneously.

3. A skin-equivalent formed by the method of claims 1 or 2.

4. In a method of forming skin-equivalent, including the steps of: (a) forming a hydrated collagen lattice incorporating a living cellular contractile agent therein; (b) maintaining said lattice and said contractile agent under conditions sufficient for said agent to contract said collagen lattice to form living dermal-equivalent; (c) overgrowing keratinocyte cells upon said dermal equivalent; and (d) maintaining said dermal equivalent under conditions sufficient for growth of said living cellular contractile agent and said keratinocyte cells to thereby produce a skin-equivalent:
   the improvement wherein keratinocyte cells are grown on the surface of said dermal-equivalent by incorporating one or more punch biopsies of skin into said dermal-equivalent and maintaining said dermal-equivalent with the punch biopsies therein under conditions sufficient for keratinocyte cells from said skin biopsies to overgrow the surface of said dermal-equivalent.

5. A method of treating a wound to or disease of the skin of a recipient, comprising:
   a. forming a hydrated collagen lattice incorporating a living cellular contractile agent therein;
   b. removing one or more punch biopsies of skin from a donor;
   c. incorporating said punch biopsies removed from the donor into said hydrated collagen lattice;
   d. maintaining the hydrated collagen lattice containing said punch biopsies under conditions sufficient for the contractile cells to contract the hydrated collagen lattice and sufficient to allow keratinocyte cells from said punch biopsies of skin to overgrow the surface of said hydrated collagen lattice thereby producing a skin-equivalent for said recipient; and e. applying said skin-equivalent to the wound of said recipient.

6. A method of claim 5 wherein said recipient is a human being.

7. A method of claim 6 wherein said donor is a human being.

8. A method of claim 5 wherein said recipient and said donor comprise the same human being.

9. A method of claims 5 or 8 wherein said contractile agent comprises fibroblast cells.

10. A method of preparing skin-equivalent, comprising:

a. forming a hydrated collagen lattice incorporating a living cellular contractile agent therein;

b. maintaining the hydrated collagen lattice and said contractile agent under conditions sufficient for said agent to contract said collagen lattice to form living dermal-equivalent;

c. growing keratinocyte cells upon the surface of said dermal equivalent to form a skin-equivalent;

d. removing one or more punch biopsies from said skin-equivalent;

e. incorporating said punch biopsies into another hydrated collagen lattice containing a living cellular contractile agent;

f. maintaining said another hydrated collagen lattice containing a living cellular contractile agent and said punch biopsies under conditions sufficient for formation of another skin-equivalent therefrom; and g. optionally repeating steps d–f to produce further skin-equivalents.

* * * * *